United States Patent [19]
Barthold et al.

[11] Patent Number: 5,937,439
[45] Date of Patent: Aug. 17, 1999

[54] COMBINATION HEAD AND EYE-PROTECTIVE APPARATUS AND GOGGLES

[75] Inventors: Michael J. Barthold, Flemington; Steven Bellofatto, Closter; Louis Orotelli, Washington Township, all of N.J.

[73] Assignee: Cairns & Brother Inc., Clifton, N.J.

[21] Appl. No.: 08/872,431

[22] Filed: Jun. 10, 1997

[51] Int. Cl.[6] .................................................. A61F 9/02
[52] U.S. Cl. ............................................ 2/10; 2/5; 2/175.5
[58] Field of Search ............................... 2/5, 6.3, 10, 439, 2/426, 13, 100, 175.2, 175.5, 452; 24/200; 128/207.11

[56] References Cited

U.S. PATENT DOCUMENTS

| | | | |
|---|---|---|---|
| 3,373,444 | 3/1968 | Militello | 2/10 |
| 3,383,155 | 5/1968 | Bourke | 351/155 |
| 3,703,750 | 11/1972 | Irwin, Jr. | 2/10 |
| 3,781,915 | 1/1974 | Menold et al. | 2/10 |
| 4,193,133 | 3/1980 | Laibach et al. | 2/10 |
| 4,276,657 | 7/1981 | Montesi | 2/10 |
| 5,341,516 | 8/1994 | Keim | 2/5 |

Primary Examiner—John J. Calvert
Assistant Examiner—Tejash D Patel
Attorney, Agent, or Firm—R. Gale Rhodes, Jr.

[57] ABSTRACT

Combination head and eye-protective apparatus including a head-protective helmet provided with a brim including a rearward brim portion, and goggles including an elastic member and a mounting member mounted to the elastic member and for wedgedly engaging the rearward brim portion to mount the goggles to the helmet. Goggles including a frame having outer portions, eye-protective lens mounted in the frame, an elastic member having outer ends and a rearward central portion and a mounting member mounted to the rearward central portion of the elastic member, the outer ends of the elastic member mounted to the outer end portions of the frame.

21 Claims, 4 Drawing Sheets

COMBINATION HEAD AND EYE-PROTECTIVE APPARATUS AND GOGGLES

BACKGROUND OF THE INVENTION

This invention relates generally to new and improved combination head and eye-protective apparatus and more particularly relates to new and improved combination head-protection helmet, particularly a firefighter's helmet, and goggles. Further generally, this invention relates to new and improved goggles and more particularly relates to new and improved goggles particularly useful for being mounted to a head-protective helmet such as, for example, a firefighter's helmet.

In February 1997, the National Fire Protection Association (NFPA) approved the use of goggles by firefighters in lieu of a face shield or visor.

Accordingly, there exists a specific need in the art for combination firefighter's helmet and goggles mounted thereto, and there further exists a specific need in the art for goggles particularly useful for being mounted to a firefighter's helmet.

Combination firefighter's helmet and goggles and goggles for being mounted to a firefighter's helmet are known to the prior art. For example, such combination and goggles are disclosed in U.S. Pat. No. 5,341,516 entitled GOGGLE SUPPORT SYSTEM, patented Aug. 30, 1994, Eric Keim inventor. In the second embodiment disclosed in this patent and shown in FIGS. 3–6, goggles 15 are mounted to a helmet 19 by thumb screws 79. Referring to FIGS. 5 and 6, particularly FIG. 5, the thumb screw 79 extending from the thumb wheel 77 extends through a grommet 89 provided in the main goggle strap 41 and is threaded into a nut 85. Such mounting of the goggles 15 to the helmet 19 by the use of thumb screws 79 is at least somewhat tedious, requires considerable manual dexterity and makes it undesirably difficult to remove and replace the goggles. Accordingly, there further exists a need in the art for goggles which may be quickly and easily mounted to a firefighter's helmet and which goggles may be quickly and easily removed and replaced.

SUMMARY OF THE INVENTION

It is the object of the present invention to satisfy the foregoing need in the art.

Combination head and eye-protective apparatus satisfying such need and embodying the present invention may include a head-protective helmet provided with a brim including a rearward brim portion, and goggles including an elastic member and a mounting member mounted to the elastic member and for wedgedly engaging the rearward brim portion to mount the goggles to the helmet.

Goggles of the present invention may include a frame having outer portions, eye-protective lens mounted in the frame, an elastic member having outer ends and a rearward central portion and a mounting member mounted to the rearward central portion of the elastic member, the outer ends of the elastic member mounted to the outer end portions of the frame.

DESCRIPTION OF THE PREFERRED EMBODIMENTS

Figure 1:
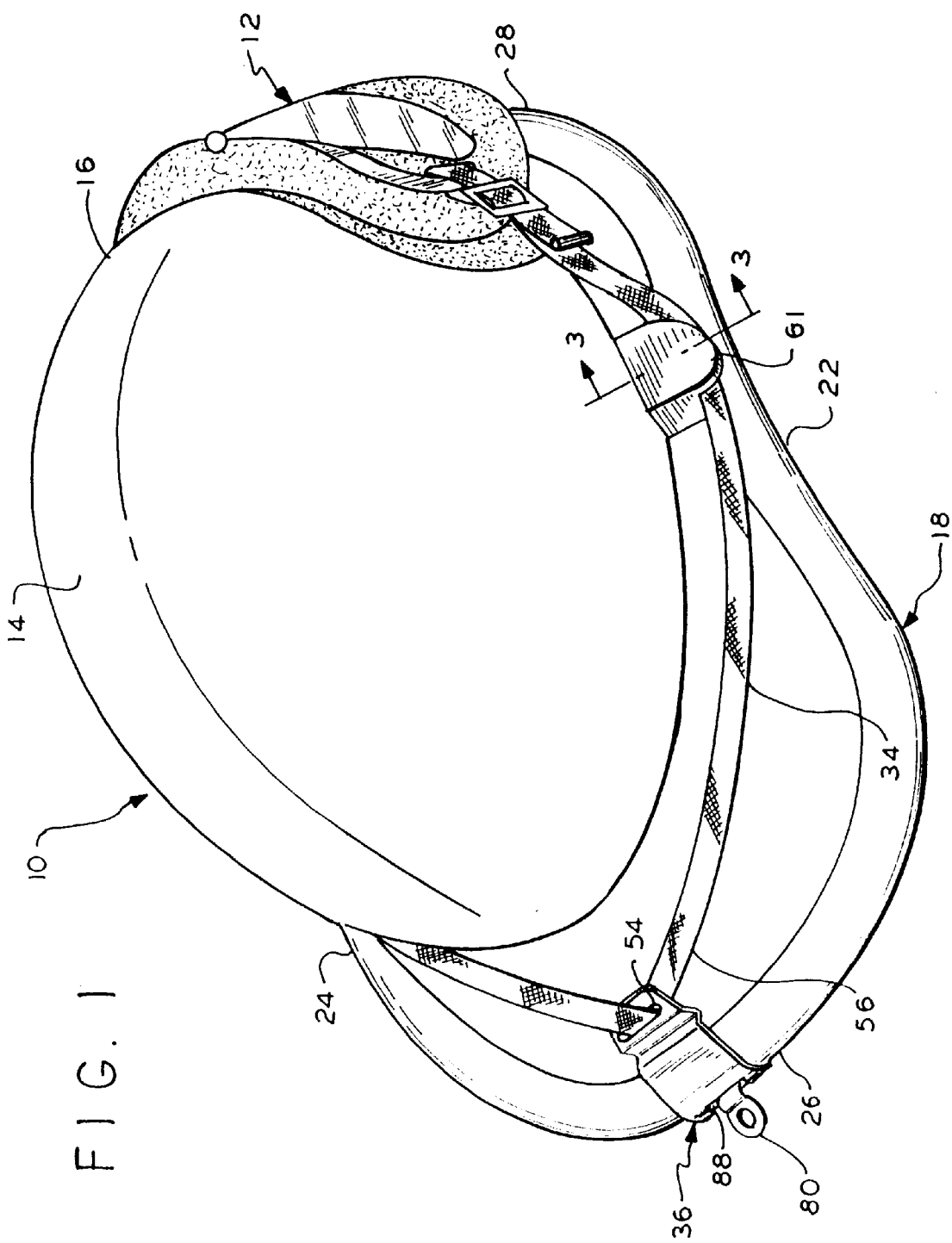
FIG. 1 is, generally, a top right side perspective view of combination head and eye-protective apparatus embodying the present invention with the head-protective helmet shown embodied as a firefighter's helmet and with the eye-protective apparatus shown embodied as goggles.
Figure 2:
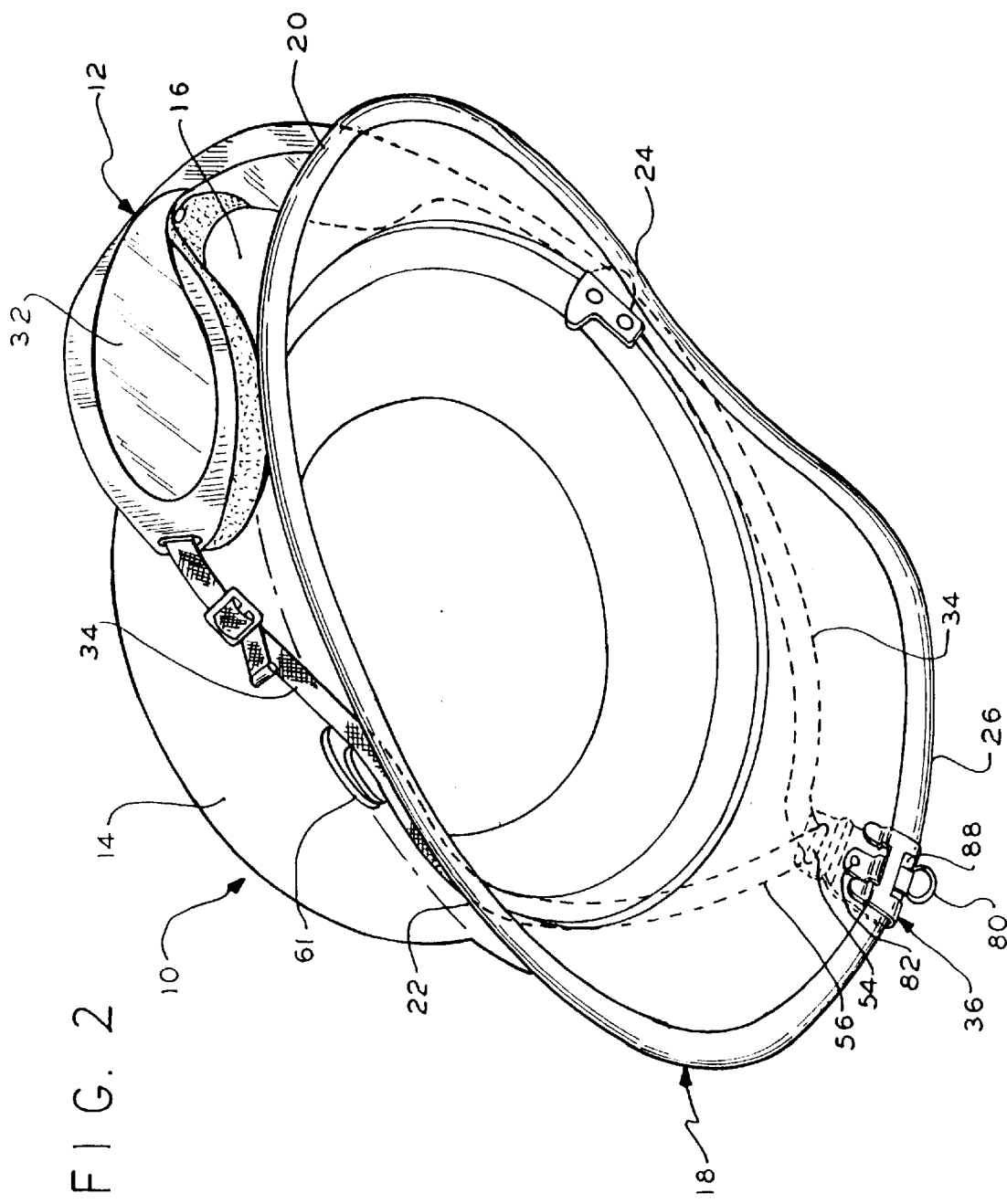
FIG. 2 is, generally, a bottom perspective view of the combination head and eye-protective apparatus shown in FIG. 1.

Referring now to FIGS. 1 and 2, combination head and eye-protective apparatus of the present invention are shown and are shown embodied as a firefighter's helmet indicated by general numerical designation 10 and goggles indicated by general numerical designation 12; however, it will be understood that such firefighter's helmet is merely by way of illustration and that the present invention is not limited to such firefighter's helmet. Helmet 10 includes a crown 14 including a forward portion 16 and a brim indicated by general numerical designation 18 including a forward portion 20, side portions 22 and 24 and a rearward portion 26.

Figure 4:
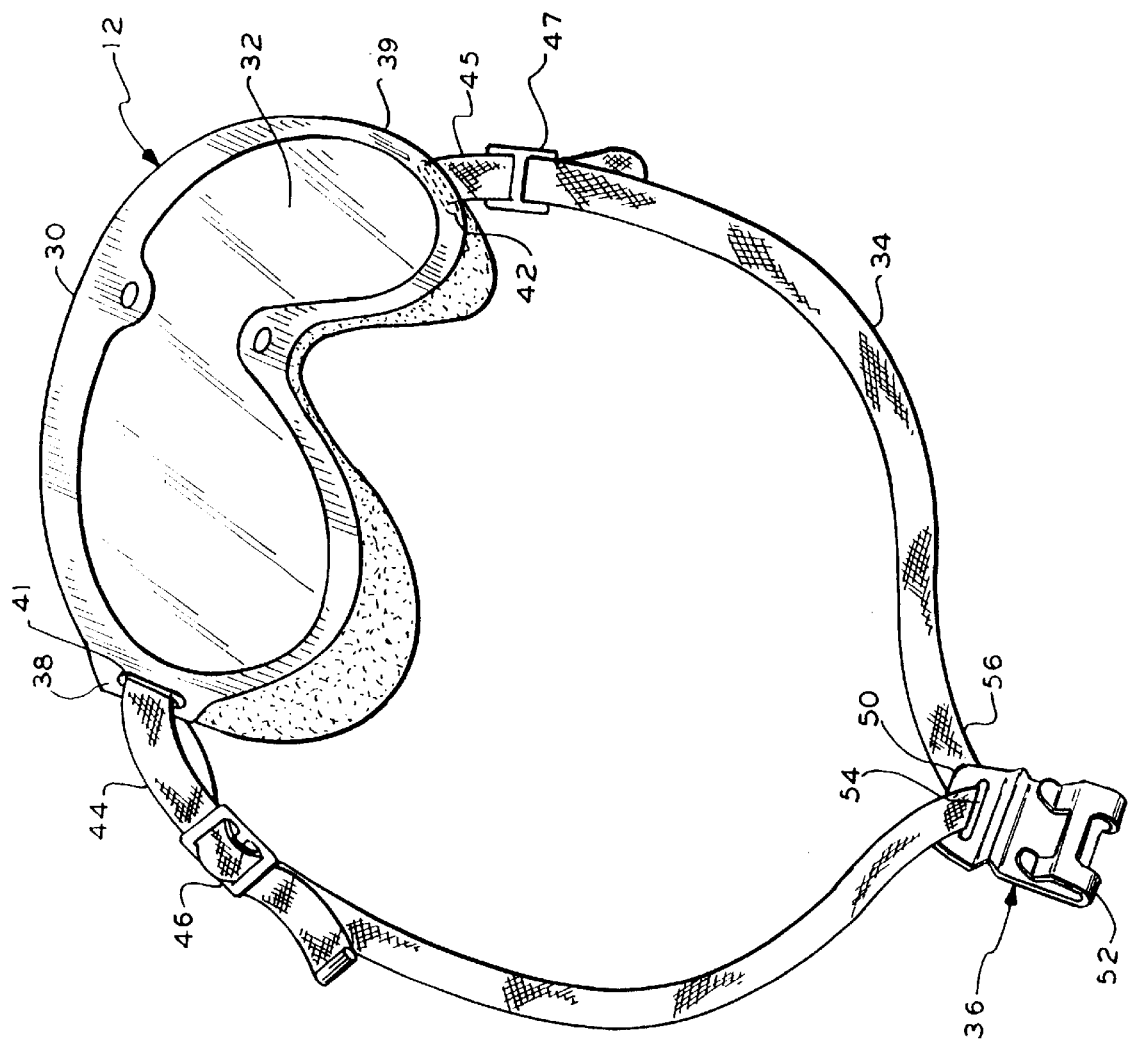
FIG. 4 is a perspective view of goggles embodying the present invention.

Referring to FIG. 4, goggles 12 include a goggle frame 30, substantially transparent eye-protective lens 32 mounted in the goggle frame, an elastic band or strap 34 and a resilient generally U-shaped spring-clip mounting member indicated by general numerical designation 36. It will be generally understood that the spring-clip 36 is generally U-shaped and is for wedgedly engaging the helmet rearward brim portion 26, FIGS. 1 and 2, to mount the spring-clip mounting member to the rearward brim portion 26 and to thereby mount the goggles 12 to the helmet 10.

As shown in FIG. 4, the goggle frame 30 includes outer end portions 38 and 39 provided respectively with openings 41 and 42. The elastic member 34 includes outer end portions 44 and 45 which are respectively looped through the frame openings 41 and 42 and then threaded back and threaded through suitable slide buckles 46 and 47, of the type known to the art for adjusting or varying the length of the elastic strap 34, to mount the elastic strap ends 44 and 45 to the goggle frame 30. At least the outer portion of the goggle frame 30 may be made of suitable soft material, such as rubber or suitable flame retardant thermoplastic elastomer of the type known to the art, to facilitate sealing of the goggle frame 30 around the eyes of the helmet wearer upon the elastic strap 34 being contracted.

The spring-clip mounting member 36, shown generally in FIG. 4, includes an upper portion 50 and a lower portion 52. The upper portion 50 is provided with an opening 54 through which the central rearward portion 56 of the elastic strap 34 extends to connect the elastic strap to the spring-clip mounting member 36 or, as viewed differently, to mount the spring-clip mounting member 36 to the elastic strap 34.

In FIGS. 1 and 2, the goggles 12 are shown in the stowed position against the forward helmet portion 16 of the helmet crown 14 and it will be understood that the elastic strap 34 is sufficiently contractible to hold and stow the goggle frame 30 and protective lens 32 against the forward crown portion 14. It will be further understood that the elastic strap 34 is sufficiently stretchable to permit the goggle frame 30 and lens 32 to be pulled forwardly and downwardly over the forward portion 20 of the brim 18 and the side portions 22 and 24 of the brim to permit the goggle frame and lens to be placed over the eyes of the wearer of the helmet 10. The elastic strap 34 is also sufficiently contractible to hold the goggle frame 30 and eye-protective lens 32 over the eyes of the helmet wearer and to seal the goggle frame 30 around the eyes of the helmet wearer. Further, the elastic strap 34 is sufficiently stretchable to permit the above-described procedure to be reversed by permitting the goggle frame 30 and eye-protective lens 32 to be pulled upwardly over the brim forward portion 20 and over the brim side portions 22 and 24 to place the frame and lens in the above-described stowed position against the forward portion 16 of the helmet crown 14.

Figure 3:
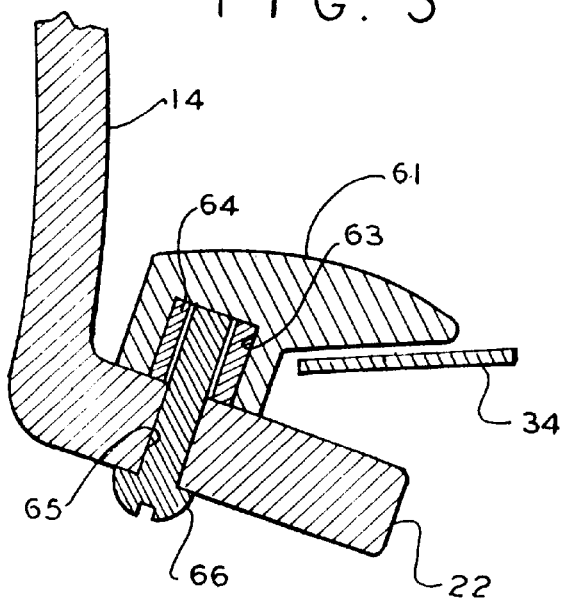
FIG. 3 is a cross-sectional view taken generally along the line 3—3 in FIG. 1 in the direction of the arrows.

To assist in maintaining the goggles frame 30 and eye-protective lens 32 in the stowed position against the helmet forward crown portion 16, the helmet side portions 22 and 24 may be provided, respectively, with generally opposed elastic strap retaining members 61 and 62; only elastic strap retaining member 61 is shown in FIGS. 1 and 2, but it will be understood that elastic strap retaining member 62 is provided on the helmet side portion 24 opposite the elastic strap retaining member 61. As will be understood by reference to FIG. 3 and representative retaining member 61, the retaining members are generally outwardly extending, inverted L-shaped members suitably mounted to the sides of the helmet brim as shown in detail in FIG. 3. As will be understood from FIG. 3, the retaining member 61 may be provided with an opening 63 in which is mounted an internally threaded insert 64, suitably mounted in the opening 63 such as in an interference or press fit, and the brim side portion 22 may be provided with an opening 65 through which a threaded member 66 is inserted to threadedly engage the threaded insert 64 to mount the retaining member 61 to the brim side portion 22. The elastic strap 34 is shown in cross section in FIG. 3 retained by the retaining member 61 upon, as noted above, the goggles 12 being in the stowed position as shown in FIGS. 1 and 2.

Figure 5:
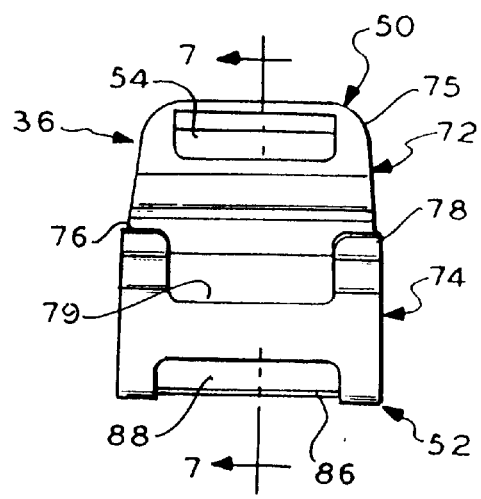
FIG. 5 is a front elevational view of spring-clip mounting member of the present invention.
Figure 6:
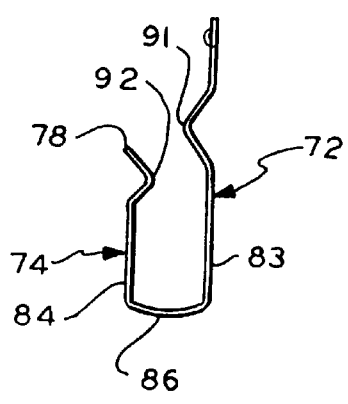
FIG. 6 is a right side view of the spring-clip mounting member shown in FIG. 5.
Figure 7:
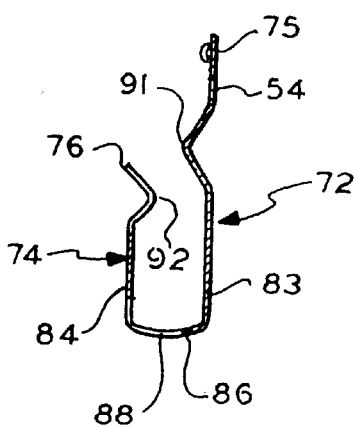
FIG. 7 is a vertical cross-sectional view taken generally along the line 7—7 in FIG. 5 in the direction of the arrows.

Referring now to the detailed structure of the spring-clip 36 and to FIGS. 5–7, spring-clip mounting member 36 includes the above-noted upper portion indicated by general numerical designation 50 and the above-noted lower portion indicated by general numerical designation 52. Further, the spring-clip mounting member 36 includes substantially parallel first and second portions indicated respectively by general numerical designations 72 and 74. The upper portion 75 of first portion 72, note FIGS. 5 and 7, is provided with the opening 54 for receiving the central rearward portion 56 of the elastic strap 34, note FIGS. 1 and 2, to mount the spring-clip mounting member 36 to the elastic strap 34. The second portion 74 of the spring-clip mounting member 36 includes a pair of substantially co-planar spaced apart legs 76 and 78 interconnected by a transverse member 79 which provides structural stability and integrity to the legs 76 and 78 and maintains them in their relative positions shown in FIG. 5. Referring again to FIGS. 1 and 2, it will be noted that the rearward brim portion 26 of the helmet 10 is provided with a helmet mounting member or ring 80 mounted pivotally to the rearward brim portion by the member 82 shown in FIG. 2. The helmet mounting member 80 is for mounting the helmet 10 to a support such as support typically found at a fire station. Referring again to the spring-clip mounting member 36, and to FIGS. 5–7, it will be noted that the respective lower portions 83 and 84 of the first and second portions 72 and 74 are interconnected, note particularly FIG. 6, by an outwardly curved, integrally formed, transverse member 86 provided with an opening 88 for receiving the helmet mounting member 80, note particularly FIGS. 1 and 2, and for permitting the helmet mounting member 80 to pass therethrough as the spring-clip mounting member is wedged into engagement with the rearward brim portion 26.

Referring further to FIGS. 5–7, and in particular to FIGS. 6 and 7, it will be noted that the first portion 72 is provided with an inwardly extending portion 91 and that the second portion 74 is provided with an inwardly extending portion 92 for enhancing the wedged engagement between the spring-clip mounting member 36, note FIGS. 1 and 2, and the rearward brim portion 26 of the helmet 10. The spring-clip mounting member 36 may be made of a suitable resilient material such as suitable spring steel and may be made by suitable metal stamping and bending operations as known to the art for forming spring steel into the shape of the spring-clip mounting member 36 shown in FIGS. 5–7.

The goggle frame 30 and the eye-protective lens 32, FIG. 4, may be, for example, the 450 rubber goggles available from the H.L. Bouton Co., Inc. of Buzzards Bay, Mass. 02532. The elastic strap 34 may be made of NOMEX covered NEOPRENE available from Fall River Weaving, Inc., Fall River, Mass. The retaining members 61 and 62 may be made, for example, of a suitable glass-filled thermoplastic material having a melt temperature of about 580° F. of the type of such material as known to the art.

It will be understood by those skilled in the art that many variations and modifications may be made in the present invention without departing from the spirit and the scope thereof.

What is claimed is:

1. Combination head and eye-protective apparatus, comprising:
    a head-protective helmet provided with a brim including a rearward brim portion; and
    goggles including a frame having outer end portions, eye-protective lens mounted in said frame, an elastic member having outer ends and a central rearward portion and a spring-clip mounting member including first and second portions, said first portion provided with an opening through which said central rearward portion of said elastic member extends to mount said spring-clip mounting member to said elastic member, said outer ends of said elastic member mounted to said outer end portions of said frame, and said second portion of said spring-clip mounting member for wedgedly engaging said rearward brim portion to mount said goggles to said helmet.

2. The combination according to claim 1 wherein said spring-clip mounting member is made of resilient material and is generally U-shaped.

3. The combination according to claim 1 wherein said brim also includes brim side portions and wherein said brim side portions are provided with retaining members for assisting in retaining said elastic member on said helmet upon said frame and lens being in a stowed position on said helmet.

4. Combination head and eye-protective apparatus, comprising:
    a head-protective helmet provided with a brim including a rearward brim portion;
    goggles including a frame having outer end portions, eye-protective lens mounted in said frame, an elastic member having outer ends and a central rearward portion and a spring-clip mounting member mounted to said central rearward portion of said elastic member, said outer ends of said elastic member mounted to said outer end portions of said frame, said spring-clip mounting member for wedgedly engaging said rearward brim portion to mount said goggles to said helmet, said spring-clip mounting member being made of resilient material and being generally U-shaped, said spring-clip mounting member including substantially parallel first and second portions having respective upper and lower portions, said upper portion of said first portion provided with a first opening through which said central rearward portion of said elastic member extends to mount said spring-clip mounting member to said elastic member and said second portion including a pair of substantially co-planar, spaced apart legs interconnected by a transverse member.

5. The combination according to claim 4 wherein at least one of said first and second portions is provided with an inwardly extending portion to enhance the wedged engagement between the spring-clip mounting member and said rearward brim portion of said helmet.

6. The combination according to claim 5 wherein each of said first and second portions is provided with an inwardly extending portion to enhance the wedged engagement between the spring-clip mounting member and the rearward brim portion of the helmet.

7. The combination according to claim 4 wherein said rearward brim portion is provided with a helmet mounting member for mounting said helmet to a support, and wherein said lower portions of said first and second portions are interconnected by an outwardly curved integrally formed transverse member provided with a second opening for receiving said helmet mounting member and for permitting said helmet mounting member to pass therethrough as said spring-clip mounting member is wedged into engagement with said rearward brim portion of said helmet.

8. Combination head and eye-protective apparatus, comprising:
   a head-protective helmet including a crown having a forward portion and an outwardly and downwardly extending brim including a forward brim portion, side brim portions and a rearward brim portion; and
   goggles including a frame having outer end portions, eye-protective lens mounted in said frame, an elastic member having outer ends, and a mounting member including a generally U-shaped resilient portion including substantially parallel first and second portions having respective upper and lower portions, said upper portion of said first portion provided with a first opening through which said central rearward portion of said elastic member extends to mount said mounting member to said elastic member and said second portion including a pair of substantially co-planar spaced apart legs interconnected by a transverse member, said elastic member including a central rearward portion and said outer ends of said elastic member connected to said outer end portions of said frame, said first and second portions for wedgedly engaging said rearward brim portion to mount said goggles to said brim, said elastic band being sufficiently contractible to hold and stow said frame and said lens against said forward portion of said crown when said goggles are not in use and being sufficiently contractible to hold said frame and lens over the eyes of a wearer of the helmet and being sufficiently stretchable to permit said frame and said lens to be pulled forwardly and downwardly over said brim side forward portions to place said goggles over the eyes of a wearer of said helmet.

9. The combination according to claim 8 wherein said rearward brim portion is provided with a helmet mounting member for mounting said helmet to a support, wherein said lower portions of said first and second portions are interconnected by an outwardly curved, integrally formed transverse member provided with a second opening for receiving said helmet mounting member and for permitting said helmet mounting member to pass therethrough as said mounting member is wedged into engagement with said rearward brim portion of said helmet.

10. The combination according to claim 8 wherein one of said first and second portions includes an inwardly extending portion for enhancing the wedged engagement between said mounting member and said rearward brim portion.

11. The combination according to claim 8 wherein each of said first and second portions includes an inwardly extending portion for enhancing the wedged engagement between said mounting member and said rearward brim portion.

12. The combination according to claim 8 wherein said side brim portions are provided with retaining members for assisting in retaining said elastic member on said helmet upon said frame and lens being stowed against said forward portion of said crown.

13. The combination according to claim 12 wherein said retaining members are generally outwardly extending, inverted L-shaped members mounted to and extending upwardly from said side brim portions.

14. Goggles, comprising:
   a frame having outer portions, eye-protective lens mounted in said frame, an elastic member having outer ends and including a central rearward portion and a spring-clip mounting member including a first portion and a second portion, said first portion provided with an opening through which said central rearward portion of said elastic member extends to mount said elastic member to said spring-clip mounting member and said second portion being an inwardly extending U-shaped resilient portion, and said outer ends of said elastic member mounted to said outer portions of said frame.

15. Goggles, comprising:
   a frame having outer end portions, eye-protective lens mounted in said frame, an elastic member having outer ends and a central rearward portion and a spring-clip mounting member provided with an opening through which said central rearward portion of said elastic member extends to mount said elastic member to said spring-clip mounting member, and said outer ends of said elastic member mounted to said outer portions of said frame, said spring-clip mounting member including substantially parallel first and second portions having respective upper and lower portions, said first portion provided with a first opening through which said central rearward portion of said elastic member extends to mount said spring-clip mounting member to said elastic member and said second portion including a pair of substantially co-planar spaced apart legs interconnected by a transverse member.

16. The goggles according to claim 15 wherein one of said first and second portions includes an inwardly extending portion.

17. The goggles according to claim 15 wherein each of said first and second portions includes an inwardly extending portion.

18. Goggles for being mounted to a head-protective helmet provided with a brim including a rearward brim portion, comprising:
   a frame having outer end portions, eye-protective lens mounted in said frame, an elastic member having outer ends connected to said outer end portions of said frame, and a mounting member provided with an opening and including a resilient generally U-shaped portion, said elastic member including a central rearward portion extending through said opening to mount said elastic member to said spring-clip mounting member, and said U-shaped portion of said mounting member for wedgedly engaging the rearward brim portion of the head-protective helmet to mount said goggles to the head-protective helmet.

19. Goggles for being mounted to a head-protective helmet provided with a brim including a rearward brim portion, comprising:

a frame having outer end portions, eye-protective lens mounted in said frame, an elastic member having outer ends, and a mounting member including a resilient generally U-shaped portion, said elastic member including a central rearward portion and said outer ends of said elastic member connected to said outer end portions of said frame, said mounting member mounted to said central rearward portion of said elastic member and said U-shaped portion of said mounting member for wedgedly engaging the rearward brim portion of the head-protective helmet to mount said goggles to the head-protective helmet, said mounting member including substantially parallel first and second portions having respective upper and lower portions, said first portion being provided with a first opening through which said central rearward portion of said elastic member extends to mount said spring-clip mounting member to said elastic member and said second portion including a pair of substantially co-planar spaced apart legs interconnected by a transverse member.

20. The goggles according to claim 19 wherein one of said first and second portions is provided with an inwardly extending portion for enhancing the wedged engagement between said mounting member and the rearward brim portion of the helmet.

21. The goggles according to claim 19 wherein each of said first and second portions is provided with an inwardly extending portion for enhancing the wedged engagement between said mounting member and the rearward brim portion of the helmet.

* * * * *